United States Patent
Pospisilik

(10) Patent No.: US 6,727,367 B2
(45) Date of Patent: Apr. 27, 2004

(54) PROCESS FOR RESOLUTION OF 2-AMINO-6-PROPYLAMINO-4,5,6,7-TETRAHYDROBENZTHIAZOLE AND COMPOUNDS THEREFOR

(75) Inventor: Karel Pospisilik, Brno (CZ)

(73) Assignee: Synthon BV, Nijmegen (NL)

( * ) Notice: Subject to any disclaimer, the term of this patent is extended or adjusted under 35 U.S.C. 154(b) by 52 days.

(21) Appl. No.: 09/953,870

(22) Filed: Sep. 18, 2001

(65) Prior Publication Data

US 2002/0103240 A1 Aug. 1, 2002

(30) Foreign Application Priority Data

Sep. 18, 2000 (ES) .......................................... 200002262

(51) Int. Cl.[7] ............................................. C07D 277/82
(52) U.S. Cl. ....................................................... 548/164
(58) Field of Search ........................................... 548/164

(56) References Cited

U.S. PATENT DOCUMENTS

| | | | |
|---|---|---|---|
| 4,843,086 A | | 6/1989 | Griss, deceased et al. |
| 4,886,812 A | * | 12/1989 | Griss et al. ................. 514/321 |

FOREIGN PATENT DOCUMENTS

| | | |
|---|---|---|
| EP | 0 186 087 A1 | 7/1986 |
| EP | 0 207 696 A1 | 1/1987 |

OTHER PUBLICATIONS

Journal of Pharmaceutical Science, Jan. 1977, vol. 66, No. 1.*

Journal of Medicinal Chemistry, 1987, vol. 30, No. 3, pp. 494–498: "Dopamine Autoreceptor Agonists: Resolution and Pharmacological Activity of 2,6–Diaminotetrahydrobenzothiazole and an Aminothiazole Analogue of Apomorphine," by Claus S. Schneider and Joachim Mierau.

* cited by examiner

Primary Examiner—Joseph K. McKane
Assistant Examiner—Kamal Saeed
(74) Attorney, Agent, or Firm—Fleshner & Kim, LLP

(57) ABSTRACT

A process for resolving or enriching (R,S) 2-amino-6-propylamino-4,5,6,7-tetrahydrobenzothiazole (pramipexole) into optical isomers uses a monovalent salt thereof, e.g. pramipexole monohydrochloride, as a substrate. The monovalent salt is treated with an optically active acid, e.g. with L(+)-tartaric acid, to yield a diastereomeric mixed salt. The mixed salt is subjected to fractional crystallization to yield an optically enriched mixed salt. The mixed salt can be treated with base to liberate the desired isomer of pramipexole.

32 Claims, No Drawings

PROCESS FOR RESOLUTION OF 2-AMINO-6-PROPYLAMINO-4,5,6,7-TETRAHYDROBENZTHIAZOLE AND COMPOUNDS THEREFOR

BACKGROUND OF THE INVENTION

The present invention relates to a process for the resolution of (R,S) 2-amino-6-propylamino-4,5,6,7-tetrahydrobenzothiazole into optically enriched and/or optically pure enantiomers and to compounds useful therein.

2-amino-6-(substituted)amino-4,5,6,7-tetrahydrobenzothiazoles having the general formula (A):

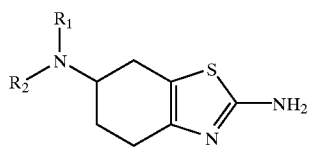

(A)

wherein $R_1$ is hydrogen, alkyl or aralkyl group and $R_2$ is hydrogen, are known pharmaceutical active agents. See for example U.S. Pat. No. 4,843,086 and EP 186087 where these and other tetrahydrobenzthiazole derivatives are taught to be useful in treating schizophrenia, Parkinson's disease or Parkinsonism, and/or hypertension. Among the known compounds is (S)-2-amino-6-propylamino-4,5,6,7-tetrahydrobenzothiazole of the formula (B) which is more commonly known as pramipexole.

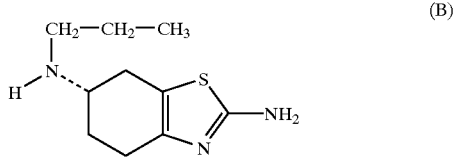

(B)

Pramipexole is commercially sold as a dihydrochloride salt in a peroral formulation.

The compounds of formula (A) have one asymmetric carbon and they may exist either as a single enantiomer or in a mixed or racemic form. The pharmacological activity of compounds of formula (A) is generally connected only or mainly with one isomer thereof. Accordingly, pramipexole is marketed as a single S(−) enantiomer; the dopaminergic activity of the (S) isomer is twice as high as that of the (R) enantiomer.

One general process for preparing compounds of the above formula (A) applicable to a synthesis of pramipexole (general method A) is suggested in U.S. Pat. No. 4,843,086, EP 186087 and EP 207696. The process comprises ring halogenation (preferably bromination) of a substituted aminoketone (C) and the condensation of the so obtained alpha-halogenaminoketone (D) with thiourea to form a 2-aminotetrahydrobenzthiazole ring, as shown in the following scheme:

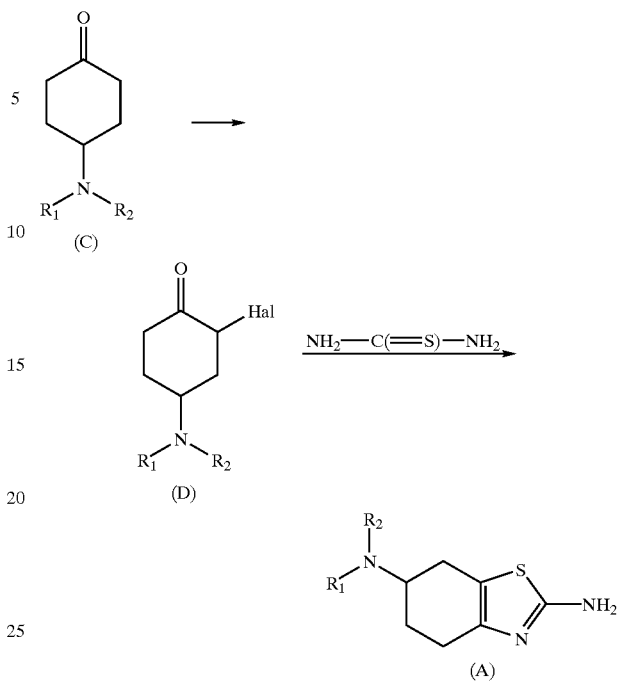

In practice, compounds of formula (A) comprising a primary amino group or a secondary alkylamino group cannot be prepared from the corresponding compounds of formula (C) directly due to the reactivity of the amino/alkylamino group during preparation, halogenation and cyclization of compounds (C).

The following three variants of the indirect synthetic process leading to pramipexole, i.e. to a compound of formula (A), wherein $R_1$ is propyl and $R_2$ is hydrogen, may be derived from the above general method A.

a) Propylation of a compound (A) wherein both $R_1$ and $R_2$ is hydrogen.

The starting compound of formula (A), wherein both $R_1$ and $R_2$ are hydrogen, may be prepared from a compound (C) wherein either $R_1$ is an amino-protective group such as an acyl or alkoxycarbonyl group and $R_2$ is hydrogen or $R_1$,—$R_2$ together form an imino-protective group such as phthalimidogroup; after halogenation and condensation with thiourea, the protective group is removed in a separate step.

b) Reduction of a carbonyl moiety in a compound of formula (A) wherein $R_1$ is a propionyl group and $R_1$ is hydrogen.

A compound of formula (A), wherein $R_1$ is a propionyl group and $R_2$ is hydrogen, may be prepared from a compound (C) wherein $R_1$ is a propionyl group and $R_2$ is hydrogen.

c) Bromination and cyclization of a compound (C) wherein $R_1$ is a propyl group and $R_2$ is a protective group with subsequent removal of the protective group by hydrolysis.

The starting compound (C) may be prepared from a commercially available p-aminocyclohexanol in three steps.

It is apparent that the variant b) is the most straightforward one for production of pramipexole as it does not require introduction and removal of a protective group; instead, the propionyl group serves as a protective group and it is also a direct precursor for the desired propyl group. The corresponding starting compound (C) is however not commercially available and must be prepared in advance.

However, the variants of the above general method A prepare only a racemate. Accordingly, if applied to the synthesis of pramipexole, the above process yields R,S(±)-2-amino-6-propylamino-5,6,7,8-tetrahydrobenzthiazole, which will be further, whenever appropriate, called "racemic pramipexole."

The above-mentioned patents acknowledge that the produced racemic compound of the general formula (A) may be resolved into single enantiomers by classical methods such as chromatography on a chiral phase or fractional crystallization of a salt with an optically active acid. However, even though the S(−) enantiomer of pramipexole was disclosed and characterised therein, no information is provided how it was prepared; i.e., whether it was prepared by a resolution of racemic pramipexole or from some optically active precursor. Further, no information is provided on how to produce the S(−) enantiomer of pramipexole.

An example of a process for producing optically pure pramipexole was disclosed later by Schneider and Mierau in J.Med.Chem 30, 494 (1987). The authors used the resolution of racemic 2,6-diamino-4,5,6,7-tetrahydrobenzthiazole (compound (A), $R_1=R_2=H$) into enantiomers by fractional crystallization of salts with L(+) tartaric acid. Following the resolution, the corresponding single enantiomer of the resolved diamino-precursor was converted to (−)pramipexole by a two-step propylation comprising a reaction with propionanhydride followed by reduction of the propionyl intermediate.

In conclusion, the known process for preparing optically pure pramipexole by the general method A is the variant a) in the version of Schneider and Mierau. But, this method suffers from several drawbacks including its length and undesirable economics. Thus, there exist a need for a more straightforward production process leading to S(−) pramipexole.

Such a more straightforward process may be the variant b) of the above process; however, it may be commercially interesting only if a feasible process of resolution of the so produced racemic pramipexole into (−)pramipexole is found. As of yet, such a process has not been described.

In ES P200002262, a right of priority therefrom being claimed under 35 U.S.C. §119 in the present application and the entire contents of which are incorporated herein by reference, another process is disclosed for preparing compounds of formula (A) and especially pramipexole, (general method B), said process being outlined in the following scheme.

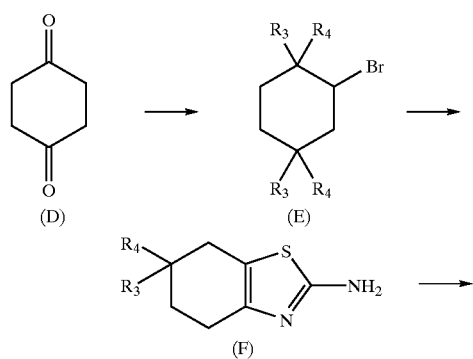

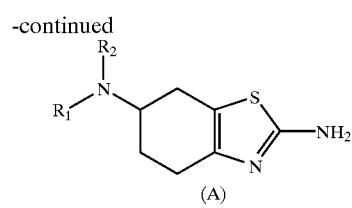

The process comprises selective monobromination of 1,4-cyclohexandione (D) in an alcoholic solvent to produce a compound of formula (E) wherein $R_3$ and $R_4$ are either the same and each of them represents an alkoxy group of 1–4 carbons or they together form a $C_2$–$C_5$ alkylenedioxy group or an oxo-group; a condensation thereof with thiourea to produce a compound of formula (F) wherein $R_3$ and $R_4$ are as defined above; and a reaction of the compound (F) with a suitable amine under conditions of reductive amination.

This general method B allows for the production of pramipexole substantially enriched by the desired S(−) enantiomer, e.g. by using a chiral catalyst for the reductive amination to propylamine or using a chiral amine convertible to propylamine as a reagent in the reductive amination. However, it would be further desirable to have a method for directly improving the optical purity of the resulting pramipexole in case the purity is insufficient.

SUMMARY OF THE INVENTION

The present invention relates to the resolution of pramipexole and to the compounds used therein. In particular, one aspect of the invention relates to a monobasic acid addition salt of 2-amino-6-propylamino-4,5,6,7-tetrahydrobenzthiazole, having the general formula (1)

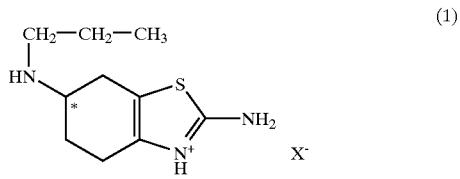

wherein X is a monovalent anion derived from an acid.
Another aspect of the invention relates to a mixed acid addition salt of 2-amino-6-propylamino 4,5,6,7-tetrahydrobenzthiazole, having the general formula (2):

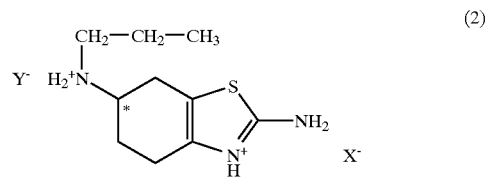

wherein X is a monovalent anion derived from an acid and Y is an anion derived from an optically active acid.

Another aspect of the invention relates to a process that comprises reacting in a solvent a mixture of (R) and (S) monobasic acid addition salts of 2-amino-6-propylamino-4,5,6,7-tetrahydrobenzthiazole having the formula (1)

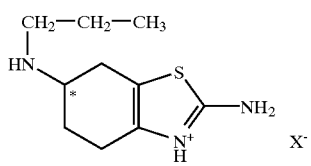

(1)

wherein X is a monovalent anion derived from an acid, with an optically active acid to form (R) and (S) diastereomeric mixed salts having the formula (2)

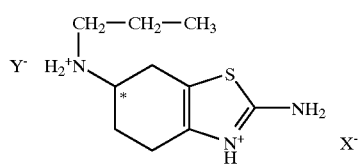

(2)

wherein X is a monovalent anion derived from an acid and Y is an anion derived from the optically active acid; and preferentially precipitating one of the (R) and (S) diastereomers from the solvent to form separated optically enriched (R) and (S) diastereomers. Either of the enriched diastereomer can be treated with base to form an enriched and/or pure (R)- or (S)-2-amino-6-propylamino-4,5,6,7-tetrahydrobenzthiazole enantiomer. The optically enriched/purified enantiomer can be reacted with an acid to form an acid addition salt. This is especially useful for forming (S)-2-amino-6-propylamino-4,5,6,7-tetrahydrobenzthiazole dihydrochloride.

DETAILED DESCRIPTION OF THE INVENTION

Experiments in resolving racemic pramipexole using fractional crystallization of diastereomeric salts of pramipexole formed with optically active acids as suggested in EP 186087 revealed that the degree of enrichment of the desired enantiomer (optical yield) was low for many of the conventional acids; i.e., ditoluyl-D-tartaric, L-mandelic and abietic acid. The resolution of racemic pramipexole into optical isomers using L(+) tartaric acid and employing "classical" conditions of optical resolution, i.e. treatment of free base of racemic pramipexole with L(+)-tartaric acid in a solvent, precipitation of the tartrate salt and decomposition of the salt, is described in Example 6 of ES P200002262. While operable, the optical yield of the product was still not ideal for commercial production as several recrystallizations would be necessary to get the product to the desired optical purity. Specifically, the specific optical rotation of pramipexole dihydrochloride obtained by the above method was $[\alpha]_D = -48°$ while the described value of optical rotation of the same product with 99.5% optical purity prepared by the indirect method of Schneider & Mierau should be $[\alpha]_D = -65°$.

Moreover, further studies have shown that the procedure is largely inconsistent when repeated and in most solvents the tartrate salt is not formed. Instead, a hemitartrate of pramipexole, i.e. a salt having 2:1 molar ratio between pramipexole and L-tartaric acid, is formed. After liberation of pramipexole base from such hemitartrate salt, it was found that the product is still essentially a racemate.

The molecule of pramipexole has two basic nitrogens able to form acid addition salts with optically active acids. Without wishing to be bound, it is theorized that the thiazole-ring nitrogen is the preferred site to form a cation which is paired with the anion of an optically active acid. Unfortunately, the thiazole nitrogen is situated, in respect to the chiral carbon, on the opposite side of the molecule. The chiral centre is probably too distant from the centre of salt formation and, as a result, the produced salts of the respective optical isomers may have negligible differences in solubility.

However, it has now been found with surprise that if the racemic pramipexole is first converted into an acid addition salt with one equivalent of an acid, i.e. into a salt wherein the basicity of one nitrogen is neutralized by an acid (hereinafter "monobasic salt"), such salt still may form a mixed salt with an optically active acid and such mixed salt can exhibit the desired solubility differential between the optical isomers of pramipexole.

The structure of the monobasic salts of the present invention is represented by general formula (1)

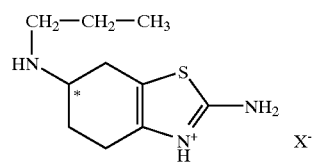

(1)

wherein X is a monovalent anion derived from an acid. The anion X is derived from an organic or inorganic acid and preferably is derived from a non-optically active acid, especially a non-optically active organic acid. Nonetheless, X can be derived from an optically active acid, especially if the acid does not effectively resolve the resulting diastereomers. Examples of suitable acids from which X can be derived include hydrochloric, hydrobromic, acetic, benzoic, methane sulfonic, ethane sulfonic, trifluoromethane sulfonic, benzene sulphonic and p-toluene sulfonic acids. Specific examples of monobasic salts of the invention are pramipexole monohydrochloride, pramipexole monohydrobromide, pramipexole methanesulfonate, pramipexole trifluoromethanesulfonate, pramipexole p-toluenesulfonate, and pramipexole benzoate. The asterisk in the formula indicates the chiral carbon atom. The compounds of formula (1) include individual (R) and (S) enantiomers as well as mixtures thereof. In this regard, the nomenclature (R) and (S) as used throughout herein should be understood to mean the spatial orientation/configuration of the pramipexole moiety that as a free base or acid addition salt exhibits (+) and (−) optical rotation, respectively.

The structure of the mixed salts of the present invention is represented by the general formula (2)

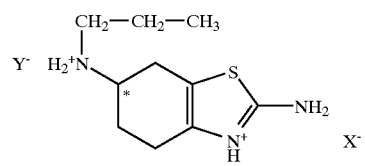

(2)

wherein X is as defined above and Y is an anion of an optically active acid. Typically, Y is an anion derived from an acid selected from the group consisting of L-tartaric acid, ditoluoyl-D-tartaric acid, and dibenzoyl-D-tartaric acid, although the optically active acids suitable for use herein are not limited thereto. Specific examples of mixed salts useful in the invention include pramipexole monohydrobromide monotartrate, pramipexole monohydrochloride monotartrate and pramipexole methanesulfonate dibenzoyl-D-tartrate. X and Y can be the same, but, preferably are different moieties. Like formula (1), the asterisk in formula (2) signifies the chiral carbon atom and the formula embraces individual (R) and (S) forms as well as mixtures thereof. For clarity, while the compounds of formula (2) are diastereomers, the (R) and (S) denotation indicates the stereo configuration of the pramipexole from which the mixed salt was formed. Because Y is derived from an optically active acid, the compounds of formula (2) are diastereomers and as such can be separated more easily by physical properties than the underlying (R) and (S) enantiomers themselves. In particular, the diastereomeric mixed acid salts are more susceptible to being separated by fractional crystallization techniques.

Accordingly, the present invention provides a process that comprises reacting in a solvent a mixture of (R) and (S) monobasic acid addition salts of the above-formula (1) with an optically active acid to form the corresponding (R) and (S) diastereomeric mixed salts of formula (2) and then preferentially precipitating one of the (R) and (S) diastereomers of formula (2) from the solvent to form separated optically enriched (R) and (S) diastereomers of formula (2). The mixture of (R) and (S) monobasic acid addition salts can be equimolar (50:50) or unequal. In some embodiments the amount of one enantiomer can be significantly greater than the amount of the other enantiomer, especially if the process is being applied to a recrystallization of a product or to a product made by an optically specific method that has insufficient purity.

The optically impure monobasic salt of pramipexole, e.g. pramipexole monohydrochloride, pramipexole monohydrobromide, or pramipexole methanesulfonate, is converted into the mixed salt of the invention by contacting the salt in a suitable solvent with a suitable optically active acid, i.e. with the acid suitable to form diastereomeric pairs of salts with pramipexole, e.g. L-tartaric acid, ditoluoyl-D-tartaric acid, dibenzoyl-D-tartaric acid etc. The solvent is preferably selected so as to facilitate the salt reaction and to allow subsequent separation of the resulting diastereomers by fractional crystallization. Suitable solvents include methanol, ethanol, acetone, dioxane, ethyl acetate, mixtures thereof, and mixtures of one or more of these solvents with water. The temperature of contact is from ambient to the boiling point of the solvent.

One of the (R) and (S) diastereomers is preferentially precipitated from the solvent. The precipitation is "preferential" in that the conditions used allow for one of the diastereomers to be precipitated to a greater extent than the other. The precipitation may be spontaneous either during or after the mixed salt-forming reaction, or it may be forced such as by cooling the mixture after contact, adding a contra-solvent, removal of a part of the solvent, or by combination of these techniques. In a preferred variant, the mixed salt of the desired (S) isomer of pramipexole is less soluble than that of the (R) isomer and thus the (S) isomer can be preferentially precipitated out of the solution.

The obtained solid mixed salt is substantially enriched by one enantiomer of pramipexole, advantageously by the (S) pramipexole. As used herein "enrichment" means that the product contains more of one of the (R) or (S) diastereomers than the starting diastereomers or starting monobasic salt. For example, if the monobasic salt contained a 50:50 mixture of (R) and (S) enantiomers, then a precipitation of a mixed salt diastereomer having an (R):(S) ratio of 30:70 would be an enriched (S) diastereomer. The degree of enrichment (optical yield) is typically at least 75%, more typically at least 80% and preferably is at least 90%. The mother liquor is likewise enriched by a salt of other enantiomer; e.g., (R) pramipexole. Optical yield may be increased by recrystallization of the desired enriched mixed salt from a suitable solvent; advantageously using the same solvent as was used for the resolution.

In an example of the advantageous embodiment of the optical resolution process of our invention, substantially racemic pramipexole monohydrochloride reacts with L-tartaric acid in a suitable solvent whereby (S) pramipexole monohydrochloride monotartrate separates out from the solution as a solid, while the salt of the (R) enantiomer remains in the solution. Similarly, substantially racemic pramipexole monohydrobromide reacts with L-tartaric acid in the same type of solvent, preferably in methanol, whereby the formed hydrobromide tartrate mixed salt of (S) pramipexole is less soluble and may be isolated as a solid. The (S) mixed salt may be separated from the reaction mixture after precipitation by ordinary methods e.g. by filtration or centrifugation. The salts may be also isolated in solvated or hydrated form.

Alternatively, the mixed salt of the desired (S) isomer can be more soluble than the (R) isomer in which case the (R) diastereomer is preferentially precipitated and the (S) diastereomer preferentially remains in the solution. This case occurs in preparing mixed salts with dibenzoyl-L-tartaric acid or with di-p-toluoyl-L-tartaric acid. The (S) diastereomer remaining in the solution may be elaborated by evaporation to obtain the desired mixed salt in solid state or may be used as it is in any subsequent process steps. Thus, because both the precipitated and the remaining dissolved diastereomers are enriched, either the precipitated or the remaining dissolved form can be used. It is preferred, however, that the (S) diastereomer be precipitated from the solvent.

Monobasic salts of any single optical isomer of pramipexole, particularly (S)-pramipexole, and more particularly (S)-pramipexole monohydrochloride, monohydrobromide or methane sulfonate as well as the mixed salts thereof with an optically active acid, particularly with L(+) tartaric acid, ditoluoyl-D-tartaric acid, dibenzoyl-D-tartaric acid and more particularly (S)-pramipexole monohydrobromide monotartrate, and (S)-pramipexole methanesulfonate dibenzoyl-D-tartrate have not been disclosed in the prior art and thus they form a specific aspect of the present invention. In general mixed salts of formula (2) having a pramipexole moiety in the (S) configuration are preferred compounds. Moreover, the optical purity of such compounds is desired to be high, for example at least 75% of the mixed salt material having the (S) pramipexole configuration, more preferably at 80%, more preferably at least 90%, still more preferably at least 95%, and still more preferably at least 99% including 99.5% or greater.

The enriched diastereomer mixed salt, either the precipitate or the solute, can be neutralized by contacting it with base to liberate the correspondingly optically enriched pramipexole. The enriched mixed salt may be advantageously isolated from the reaction mixture and optionally (re)crystallized before being contacted with base. Generally, the liberation of the desired enantiomer of pramipexole from the enriched mixed salt proceeds by contacting the salt with an equivalent of a suitable base, e.g., metal hydroxides, in a proper solvent, advantageously in water. The so formed free base of the pramipexole is isolated by ordinary methods. If water has been employed as a solvent for neutralization, (S)-pramipexole precipitates as a solid and is isolated by filtration or centrifugation. Alternately, for example in decomposition of (S)-pramipexole methane sulfonate dibenzoyl-D-tartrate, the mixed salt is contacted with water, then acidified with a stronger acid, e.g. with hydrochloric acid, and the liberated resolution agent is removed by extraction with an organic solvent e.g. with ethylacetate. (S)-Pramipexole is liberated from the aqueous layer by alkalinisation with sodium hydroxide solution. Any conventional method applicable to decomposition of pramipexole salt and liberation of pramipexole base may be employed. Advantageously, such methods are allow the isolation of, and, if advantageous, the reprocessing of the resolution agent.

The formed free base of pramipexole, especially the enriched (S) enantiomer may be further converted into an acid addition salt with a suitable acid, particularly with a pharmaceutically acceptable acid by methods known per se. In particular, the formed free base of (S)-pramipexole may be converted into pramipexole dihydrochloride.

If the optical purity of the obtained pramipexole product is not sufficient, the process may be repeated. Similarly, the process may be applied to pramipexole products from a synthesis which are insufficiently pure (S)-pramipexole. In either case, the product enriched with (S)-pramipexole is accordingly converted to a monobasic salt of formula (1), treated with an optically active acid in a suitable solvent to form diastereomeric mixed salts of formula (2), fractionally crystallizing to obtain an enriched diastereomer, and liberating the optically pure product from the desired fraction of the mixed salt.

A preferred form of the process of the present invention comprises the steps of
forming a monobasic salt of formula (1) by contacting racemic pramipexole with an equivalent of an acid in a solvent
contacting the monobasic salt with an optically active acid in a solvent to form a mixed salt of the general formula (2)
fractional crystallization of the mixed salt to yield a mixed salt substantially enriched by one optical isomer of pramipexole
liberation of pramipexole substantially enriched by one optical isomer of pramipexole by decomposition of the said enriched salt and, optionally,
converting the optically enriched pramipexole into an acid addition salt.

Preferably, the resulted enriched pramipexole is pramipexole enriched by the (S)-isomer.

The salt of undesired (R) pramipexole, either in a solution or as a solid, still represents a valuable material; it may be converted to a racemic pramipexole which may serve as a substrate for next resolution process by any suitable process of racemization. This way, overall losses of produced pramipexole are minimised.

The starting racemic or mixed (R,S)-pramipexole for the resolution process of the invention may be prepared by any process including the cited general methods above. Particularly suitable are processes based on the following schemes:

a) In a first method, racemic pramipexole is produced by a bromination of 4-propionylaminocyclohexanol followed by the condensation with thiourea according to a general method of EP 186087. The propionyl group is then reduced to propyl group by a suitable reduction agent, e.g. by in situ formed borane.

b) In a second method, 2-amino-6-oxo-4,5,6,7-tetrahydrobenzothiazole is prepared by a monobromination of 1,4-cyclohexanone in methanol followed by the condensation with thiourea in situ. The 6-oxo intermediate reacts with propylamine under presence of a reducing agent, e.g. sodium cyanoborohydride.

Racemic or enriched pramipexole may be isolated from the reaction mixture as a free base and contacted with an equivalent of suitable acid in a suitable solvent to form a monobasic salt of formula (1) or it may be directly converted into a monobasic salt of the invention in the reaction mixture by treatment of the reaction mixture with a suitable acid. The monobasic salts may be used in the process of the invention without isolation from the reaction mixture or, preferably, they may be isolated in a solid state, optionally in solvated or hydrated form, by conventional techniques of precipitation or crystallization followed by filtration or centrifugation. In an advantageous embodiment of the process of the invention, the formed monobasic salt is isolated from the reaction mixture in a solid state prior to the contact with the optically active acid, and it may be advantageously purified, e.g. by recrystallization before being further reacted.

Optically pure or substantially pure (S) pramipexole, acid addition salts thereof and particularly pramipexole dihydrochloride prepared by the process of the invention are useful in the preparation of medicaments for treatment of various diseases or conditions including schizophrenia, Parkinson's disease, Parkinsonism, hypertension, and depressions among others. It may be used alone or in combination with ergot preparation (e.g. brompcryptine or pergolide) or with levodopa. Such medicaments may be formulated for peroral, transdermal or parenteral application, for instance in a form of tablets or capsules. The formulations comprise therapeutically effective amounts of the active substance together with a pharmaceutically acceptable carriers or diluents and may be prepared by any conventional method.

An advantageous dosage form for peroral application of pramipexole prepared by the process of the invention is a tablet. Suitable tablets comprise from 0.1 to 5 mg of pramipexole dihydrochloride monohydrate, advantageously 0.125, 0.25, 0.5, 1.0, and 1.5 mg. Suitable excipients in the tablet comprise mannitol, maize starch, povidone.

Composition of tablets for peroral application of pramipexole may be as follows:

| Pramipexole (as a free base) | 0.088 mg | 0.18 mg | 0.7 mg | 0.88 mg |
|---|---|---|---|---|
| Mannitol | 49.455 mg | 61.0 mg | 121.50 mg | 162.0 mg |
| Magnesium stearate | 1.230 mg | 1.50 mg | 3.0 mg | 4.0 mg |
| Maize starch | 25.010 mg | 30.90 mg | 61.85 mg | 82.55 mg |
| Maize starch | 7.300 mg | 9.0 mg | 18.00 mg | 24.0 mg |
| Colloid silicon dioxide | 0.940 mg | 1.20 mg | 2.30 mg | 3.10 mg |
| Povidone | 0.940 mg | 1.15 mg | 2.35 mg | 3.10 mg |

Suitable tablet production methods comprise wet granulation methods. The tablets should be advantageously packed into light- and humidity protective blisters.

Controlled release compositions may be produced using pramipexole prepared by the process of the invention. In a suitable arrangement, a salt of pramipexole may be formulated into controlled-release pellets or tablet formulation, such formulation comprising a mixture of a pramipexole salt, a suitable filler, e.g. microcrystalline cellulose, and a suitable release controlling agent comprising water and/or a water-insoluble macromolecular substance such as an acrylate polymer or a modified cellulose.

The present invention is more particularly described and explained by the following examples. It is to be understood, however, that the present invention is not limited to these examples and various changes and modifications may be made without departing from the scope of the present invention.

EXAMPLES

Preparation 1: racemic pramipexole from 2-amino-6-oxo-4,5,6,7-tetrahydrobenzothiazole (General method B)

10 g of 2-amino-6-oxo -4,5,6,7-tetrahydrobenzothiazole hydrobromide was added to the mixture of 5 mL of propylamine and 125 mL of methanol under nitrogen. The mixture was stirred for 20 minutes. Then 2.7 g of sodium cyanoborohydride was added in parts during 30 minutes. The solution was acidified with 2 mL of acetic acid to the value pH=7–8. Reaction mixture was worked up after 20 hours of stirring by addition of 8 mL of HCl. Precipitated solid was removed by suction and the filtrate was evaporated to dryness. The solid residue was heated at reflux with 250 mL of ethanol for 20 minutes. Undissolved part was filtered off and the hot filtrate was concentrated under reduced pressure and cooled on an ice bath. Precipitated crystals were removed by suction and the cake was washed with cold ethanol to give 5.1 g of a product with m.p. 245–257° C.

The solid product was dissolved in 28 mL of water and the solution was alkalinized with 25% aqueous NaOH. The mixture was stirred for 2 hours and precipitated crystals were removed by suction and washed with water to give 2.7 g of the title product with m.p. 147–149° C.

Preparation 2: Racemic pramipexole from (±)-2-amino-6-propanamido-4,5,6,7-tetrahydrobenzthiazole (general method A)

6.4 g of sodium borohydride was mixed with 30 mL of anhydrous tetrahydrofuran under nitrogen. The suspension was cooled at 0–5° C. and 5.4 g of (±)-2-amino-6-propanamido-4,5,6,7-tetrahydrobenzothiazole was added to this suspension. 21 mL of boron trifluoride diethyl etherate was dropwise added to the suspension at 0–5° C. during 1.5 hour. The reaction mixture was gently warmed to 20° C. during one hour. Reaction mixture was heated at 48–50° C. for 4 hours. Then it was cooled to 0–5° C. and 50 g ice was added followed by addition of 69 mL of 36% hydrochloric acid. The reaction temperature was kept below 10° C. for 60 minutes. Then solvent was removed in vacuo and the residue was dissolved in 300 mL of water. Water solution was alkalinized by addition of 25% sodium hydroxide solution. Precipitated substance was collected by filtration, washed with water and air-dried to give 4.4 g of product. The yield 87%, m.p. 146–160° C.

Example 1

Resolution of (±)-pramipexole via Pramipexole Monohydrochloride L-tartrate a) Preparation of (±)-2-amino-6-propylamino-4,5,6,7-tetrahydrobenzthiazole monohydrochloride (pramipexole monohydrochloride)

4,2 g of (±)-2-amino-6-propylamino-4,5,6,7-tetrahydrobenzthiazole was dissolved in 15 mL of hot methanol and 1.65 mL of 36% hydrochloric acid was added. The obtained suspension was stirred, cooled and precipitated solid was filtered off. The cake was washed with cold methanol and air-dried to give 4.2 g of product with m.p. 273–282° C.

b) A mixed salt of pramipexole monohydrochloride with L(+)tartaric acid 3.00 g of (±)2-amino-6-propylamino-4,5,6,7-tetrahydrobenzthiazole monohydrochloride was dissolved in 23 mL of hot methanol and 1.80 g of L-(+)tartaric acid was added. White crystals precipitated, the mixture was cooled and crystals were removed by suction, washed with cold methanol and dried to give 2.8 g of pramipexole monohydrochloride monotartrate which was recrystallized from hot methanol to give 2.2 g of salt with m.p. 203–219° C.

c) Liberation of (S)-pramipexole free base

Pramipexole monohydrochloride monotartrate from the step b) was dissolved in 10 mL of water, the solution was cooled to 10° C., and solution of 5 g of potassium hydroxide in 10 mL of water was added. A white precipitate was formed. The mixture was stirred at 10° C. for 30 minutes and the white crystals were removed by filtration and washed with cold water. The cake was dried to give 0,95 g of the white crystals.

d) (S)-Pramipexole dihydrochloride

The crystals from the step c) were dissolved in 7 ml of ethanol and gaseous hydrogen chloride was bubbled through the solution. The mixture was stirred at 10° C. for 1 hr and the formed white crystals were removed by filtration and washed with cold methanol. The cake was dried to give 1.1 g of white crystals with m.p. 274–284° C. and $[\alpha]_D = -66.5°$ (c=1, MeOH).

Example 2

Resolution of (±)Pramipexole via Pramipexole Monohydrobromide L-tartrate a) Preparation of (±)-2-amino-6-propylamino-4,5,6,7-tetrahydrobenzothiazole monohydrobromide (pramipexole monohydrobromide)

4.00 g of (±)-2-amino-6-propylamino-4,5,6,7-tetrahydrobenzothiazole was dissolved in 10 mL of hot methanol and 2.2 mL of 48% hydrobromic acid was added. The obtained suspension was stirred, cooled and precipitated solid was filtered off. The cake was washed with cold methanol and air-dried to give 2.7 g of (±)-2-amino-6-propylamino-4,5,6,7-tetrahydrobenzothiazole monohydrobromide with m.p. 236–245° C.

b) A Mixed Salt of Pramipexole Hydrobromide with L(+)tartaric Acid 2.00 g of (±) 2-amino-6-propylamino-5,6,7,8-tetrahydrobenzothiazole mono-hydrobromide was dissolved in 20 mL of hot methanol-water mixture (100:5 v/v) and 1.02 g of L-(+)tartaric acid was added. White crystals precipitated, the mixture was cooled and crystals were removed by suction, washed with cold methanol and dried to give 0.65 g of pramipexole monohydrobromide monotartrate which was recrystallized from hot methanol to give 0.44 g of salt with m.p. 210–216° C.

c) Liberation of (S)-pramipexole free base 0.40 g of the salt from the step b) was dissolved in 8 mL of water, the solution was cooled to 10° C., and 25% aqueous sodium hydroxide was added. A white precipitate was formed. The mixture was stirred at 10° C. for 30 minutes and the white crystals were removed by filtration and washed with cold water. The cake was dried to give 0,22 g of the white crystals m.p. 136–141° C.

d) (S)-Pramipexole dihydrochloride

These crystals were dissolved in 2 ml of ethanol and gaseous hydrogen chloride was bubbled through the solution. The mixture was stirred at 10° C. for 1 hr and the white crystals were removed by filtration and washed with cold methanol. The cake was dried to give 0.34 g of white crystals with m.p. 276–285° C. and $[\alpha]_D = -62.3°$ (in methanol)

Example 3

Resolution of (±) Pramipexole via Pramipexole Methanesulfonate Dibenzoyl-D-tartrate a) Preparation of (±)-2-amino-6-propylamino-4,5,6,7-tetrahydrobenzothiazole monomethanesulfonate (pramipexole monomethanesulfonate)

11.0 g of (±) 2-amino-6-propylamino-4,5,6,7-tetrahydrobenzothiazole was dissolved in 180 mL of hot isopropanol and 3.8 mL of methanesulfonic acid was added. The formed precipitate was filtered off after cooling and dried to give 10.2 g of crystals with m.p. 227–237° C.

b) A mixed salt of pramipexole monomethanesulfonate with dibenzoyl-D-tartaric acid 5 g of (±) 2-amino-6-propylamino-4,5,6,7-tetrahydrobenzothiazole mono-methanesulfonate was dissolved in a hot mixture of 45 mL of methanol and 5 mL of water. Then 6.0 g of dibenzoyl-D-tartaric acid was added under stirring and the mixture was cooled to ambient temperature. Precipitate of crystals was removed by suction, recrystallized from methanol and dried to give 4.2 g of the product with m.p. 177–181° C.

c) (S)-pramipexole free base

The compound from the previous step was dissolved in the mixture of 30 mL of ethyl acetate, 30 mL of water and 5 mL of 36% hydrochloric acid. Water layer was twice extracted with 10 mL of ethylacetate and then it was alkalinized with sodium hydroxide solution. Precipitate was removed by suction and washed with water to give 2.50 g of the white crystals with m.p. 276–285° C. and $[\alpha]_D = -62.3°$ (in methanol)

Example 4

Resolution of (±) Pramipexole via Pramipexole Methanesulfonate Ditoluyl-D-tartrate a) A mixed salt of pramipexole monomethanesulfonate with ditoluoyl D-tartaric acid 3.6 g of pramipexole monomethanesulfonate was dissolved in a hot mixture of 30 mL of methanol and 10 mL of water. Then 3.77 g of di toluoyl-D-tartaric acid was added under stirring and the mixture was cooled to ambient temperature. Precipitate of crystals was removed by suction and dried. Yield: 4.2 g, m.p. 180–184° C.

b) (S)-pramipexole free base

The compound from the step a) was dissolved in the mixture of 30 mL of ethylacetate, 30 mL of water and 5 mL of 36% hydrochloric acid. Water layer was twice extracted with 10 mL of ethyl acetate and then it was alkalinized with sodium hydroxide solution. Precipitate was removed by suction and washed with water. (S)-Pramipexole with optical yield 48% was obtained.

The invention having been thus described, it will be readily apparent to those skilled in the art that further changes and modifications in actual implementation of the concepts and embodiments described herein can easily be made or may be learned by practice of the invention, without departing from the spirit and scope of the invention as defined by the following claims.

I claim:

1. A monobasic acid addition salt of 2-amino-6-propylamino-4,5,6,7-tetrahydrobenzthiazole, having the general formula (1)

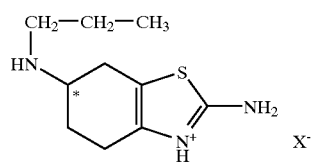

wherein X is a monovalent anion derived from an acid.

2. The salt according to claim 1, wherein the anion X is derived from an acid selected from the group consisting of hydrochloric, hydrobromic, hydroiodic, nitric, benzoic, acetic, methane sulfonic, ethane sulfonic, trifluoromethane sulfonic, benzene sulfonic, and p-toluene sulfonic acids.

3. The salt according to claim 1 wherein X is a chloride anion, a bromide anion, or a methane sulfonate anion.

4. A mixed acid addition salt of 2-amino-6-propylamino 4,5,6,7-tetrahydrobenzthiazole, having the general formula (2):

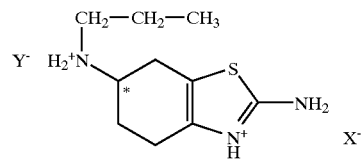

wherein X is a monovalent anion derived from an acid and Y is an anion derived from an optically active acid and wherein X and Y are different from each other.

5. The mixed salt according to claim 4, wherein Y is an anion derived from an acid selected from the group consisting of L-tartaric acid, dituoyl-D-tartaric acid, and dibenzoyl-D-tartaric acid.

6. The mixed salt according to claim 4 which is 2-amino-6-propylamino-4,5,6,7-tetrahydrobenzothiazole monohydrochloride monotartrate, 2-amino-6-propylamino-4,5,6,7-tetrahydrobenzothiazole monohydrobromide monotartrate, or 2-amino-6-propylamino-4,5,6,7-tetrahydrobenzothiazole monomethanesulfonate dibenzoyl-D-tartrate.

7. The mixed salt according to claim 4, wherein at least 80% of the 2-amino-6-propylamino-4,5,6,7-tetrahydrobenzthlazole moiety is in the (S) configuration.

8. A process which comprises:

reacting in a solvent a mixture of (R) and (S) monobasic acid addition salts of 2-amino-6-propylamino-4,5,6,7-tetrahydrobenzthiazole having the formula (1)

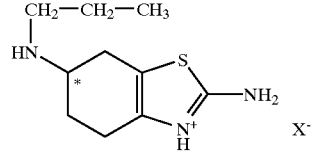

wherein X is a monovalent anion derived from an acid, with an optically active acid to form (R) and (S) diastereomeric mixed salts having the formula (2)

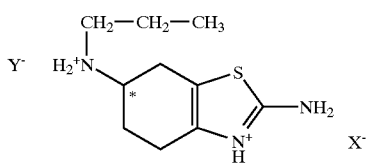

wherein X is a monovalent anion derived from an acid and Y is an anion derived from said optically active acid and wherein X and Y are different from each other; and preferentially precipitating one of said (R) and (S) diastereomers from the solvent to form separated optically enriched (R) and (S) diastereomers.

9. The process according to claim 8, wherein said precipitation occurs spontaneously during or after said reaction.

10. The process according to claim 8, wherein said precipitation is induced by reducing the temperature of the solvent.

11. The process according to claim 8, wherein said solvent is selected from the group consisting of methanol, ethanol, acetone, dioxane, ethyl acetate, mixtures thereof, and mixtures of one or more with water.

12. The process according to claim 8, wherein said mixture of (R) and (S) monobasic salts of formula (1) are selected from the group consisting of 2-amino-6-propylamino-4,5,6,7-tetrahydrobenzothiazole monohydrochloride, 2-amino-6-propylamino-4,5,6,7-tetrahydrobenzothiazole mononhydrobromide, and 2-amino-6-propylamino-4,5,6,7-tetrahydrobenzothiazole monomethanesulfonate.

13. The process according to claim 8, wherein said diastereomeric mixed salts of formula (2) are selected from the group consisting of 2-amino-6-propylamino-4,5,6,7-tetrahydrobenzothiazole monohydrochloride monotartrate, 2-amino-6-propylamino-4,5,6,7-tetrahydrobenzothiazole monohydrobromide monotartrate, and 2-amino-6-propylamino-4,5,6,7-tetrahydrobenzothiazole monomethanesulfonate dibenzoyl-D-tartrate.

14. The process according to claim 8, which further comprises treating one of said optically enriched diastereomers with base to form the corresponding optically enriched (R) or (S) 2-amino-6-propyl-4,5,6,7-tetrahydrobenzthiazole.

15. The process according to claim 14, wherein said precipitated optically enriched diastereomer is treated with said base.

16. The process according to claim 15, which further comprises isolating said precipitated optically enriched diastereomer and dissolving said isolated diastereomer in a second solvent before or during treating with said base.

17. The process according to claim 16, wherein said second solvent is water.

18. The process according to claim 15, wherein the (S) diastereomer is preferentially precipitated from said solvent and is treated with said base to form optically enriched (S)-2-amino-6-propyl-4,5,6,7-tetrahydrobenzthiazole.

19. The process according to claim 18, wherein said enriched (S)-2-amino-6-propyl-4,5,6,7-tetrahydrobenzthiazole has an optical purity of at least 98%.

20. The process according to claim 14, which further comprises reacting said enriched (R)- or (S)-2-amino-6-propyl-4,5,6,7-tetrahydrobenzthiazole with an acid to form the corresponding enriched (R)- or (S)-2-amino-6-propyl-4,5,6,7-tetrahydrobenzthiazole acid addition salt.

21. The process according to claim 19, which further comprises reacting said enriched (S)-2-amino-6-propyl-(4,5,6,7-tetrahydrobenzthiazole with hydrochloric acid to form (S)-2-amino-6-propyl-4,5,6,7-tetrahydrobenzthiazole dihydrochloride.

22. The process according to claim 8, wherein said mixture does not contain an equal amount of (R) and (S) monobasic salts.

23. The mixed salt according to claim 4, wherein the anion X is derived from an acid selected from the group consisting of hydrochloric, hydrobromic, hydroiodic, nitric, benzoic, acetic, methane sulfonic, ethane sulfonic, trifluoromethane sulfonic, benzene sulfonic, and p-toluene sulfonic acids.

24. The mixed salt according to claim 4, wherein X is a chloride anion, a bromide anion, or a methane sulfonate anion.

25. The mixed salt according to claim 5, wherein X is a chloride anion, a bromide anion, or a methane sulfonate anion.

26. The process according to claim 8, wherein the anion X is derived from an acid selected from the group consisting of hydrochloric, hydrobromic, hydroiodic, nitric, benzoic, acetic, methane sulfonic, ethane sulfonic, trifluoromethane sulfonic, benzene sulfonic, and p-toluene sulfonic acids.

27. The process according to claim 8, wherein X is a chloride anion, a bromide anion, or a methane sulfonate anion.

28. The process according to claim 8, wherein Y is an anion derived from an acid selected from the group consisting of L-tartaric acid, ditoluoyl-D-tartaric acid, and dibenzoyl-D-tartaric acid.

29. The process according to claim 28, wherein Y is an anion derived from an acid selected from the group consisting of L-tartaric acid, ditoluoyl-D-tartaric acid, and dibenzoyl-D-tartaric acid.

30. The salt according to claim 1, wherein the anion X is derived from benzene sulfonic acid.

31. The salt according to claim 30, wherein said salt is (S)-pramipexole benzenesulphonate.

32. The salt according to claim 30, wherein said salt is in solid state.

* * * * *

UNITED STATES PATENT AND TRADEMARK OFFICE
CERTIFICATE OF CORRECTION

PATENT NO. : 6,727,367 B2  Page 1 of 1
APPLICATION NO. : 09/953870
DATED : April 27, 2004
INVENTOR(S) : Pospisilik It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 52 days Delete the phrase "by 52 days" and insert -- by 0 days --

Signed and Sealed this

Sixteenth Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 6,727,367 B2  Page 1 of 1
APPLICATION NO. : 09/953870
DATED : April 27, 2004
INVENTOR(S) : Pospisilik It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 52 days Delete the phrase "by 52 days" and insert -- by 0 days --

Signed and Sealed this

Seventeenth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO. : 6,727,367 B2 Page 1 of 1
APPLICATION NO. : 09/953870
DATED : April 27, 2004
INVENTOR(S) : Pospisilik It is certified that error appears in the above-identified patent and that said Letters Patent is hereby corrected as shown below:

On the cover page, item

[*] Notice: Subject to any disclaimer, the term of this patent is extended or adjusted under 35 USC 154(b) by 0 days Delete the phrase "by 0 days" and insert -- by 52 days --

Signed and Sealed this

Twenty-eighth Day of April, 2009

JOHN DOLL
*Acting Director of the United States Patent and Trademark Office*